(12) United States Patent
Roy (10) Patent No.: US 8,048,007 B2
(45) Date of Patent: Nov. 1, 2011

(54) PROSTHETIC AND ORTHOTIC SYSTEMS USABLE FOR REHABILITATION

(75) Inventor: Kim De Roy, Antwerp (BE)

(73) Assignee: Össur hf (IS)

( * ) Notice: Subject to any disclaimer, the term of this patent is extended or adjusted under 35 U.S.C. 154(b) by 1460 days.

(21) Appl. No.: 11/346,044

(22) Filed: Feb. 2, 2006

(65) Prior Publication Data

US 2006/0173552 A1 Aug. 3, 2006

Related U.S. Application Data

(60) Provisional application No. 60/649,417, filed on Feb. 2, 2005, provisional application No. 60/721,622, filed on Sep. 29, 2005.

(51) Int. Cl.
*A61H 1/02* (2006.01)
(52) U.S. Cl. .................. 601/5; 601/33; 601/34
(58) Field of Classification Search ............... 601/33, 601/5, 23, 34, 35; 623/24, 39, 40
See application file for complete search history.

(56) References Cited

U.S. PATENT DOCUMENTS

| | | |
|---|---|---|
| 2,568,051 A | 9/1951 | Catranis |
| 3,820,168 A | 6/1974 | Horvath |
| 3,995,324 A | 12/1976 | Burch |
| 4,030,141 A | 6/1977 | Graupe |
| 4,065,815 A | 1/1978 | Sen-Jung |
| 4,179,759 A | 12/1979 | Smith |
| 4,209,860 A | 7/1980 | Graupe |
| 4,212,087 A | 7/1980 | Mortensen |
| 4,387,472 A | 6/1983 | Wilson |
| 4,521,924 A | 6/1985 | Jacobsen et al. |
| 4,558,704 A | 12/1985 | Petrofsky |
| 4,569,352 A | 2/1986 | Petrofsky et al. |

(Continued)

FOREIGN PATENT DOCUMENTS

DE 2740804 3/1978

(Continued)

OTHER PUBLICATIONS

Au S K et al., "An EMG-Position Controlled System for an Active Ankle-Foot Prosthesis: An Initial Experimental Study" Rehabilitation Robotics, 2005. ICORR 2005., 9th International Conference in Chicago, IL, USA Jun. 28-Jul. 1, 2005, Piscataway, NJ, IEEE, Jun. 28, 2005, pp. 375-379, XP008078417.

(Continued)

*Primary Examiner* — Quang D Thanh
(74) *Attorney, Agent, or Firm* — Knobbe, Martens, Olson & Bear, LLP (57) ABSTRACT

Disclosed are adjustable powered rehabilitation devices and methods for using the same to rehabilitate and/or train a user. The rehabilitation devices preferably have a plurality of selectable power settings that correspond to one or more rehabilitation-oriented actions or functions of the rehabilitation devices. For example, the power of the rehabilitation device may be selected based on a need, ability, muscle-power and/or physiological characteristics of the user. For instance, a rehabilitation device may be operated at a relatively low power setting to allow a patient to use his or her own muscle power when moving with the rehabilitation device. The rehabilitation device may also include an adjustable sensitivity level that corresponds to a user difficulty in triggering a particular rehabilitation-oriented action. The powered rehabilitation device may also temporarily be used to train a user in interacting with a passive or more conventional prosthetic device.

21 Claims, 6 Drawing Sheets

U.S. PATENT DOCUMENTS

| | | |
|---|---|---|
| 4,711,242 A | 12/1987 | Petrofsky |
| 4,776,852 A | 10/1988 | Rubic |
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards |
| 5,044,360 A | 9/1991 | Janke |
| 5,062,856 A | 11/1991 | Sawamura et al. |
| 5,062,857 A | 11/1991 | Berringer et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,181,931 A | 1/1993 | Van de Veen |
| 5,201,772 A | 4/1993 | Maxwell |
| 5,217,500 A | 6/1993 | Phillips |
| 5,219,365 A | 6/1993 | Sabolich |
| 5,252,102 A | 10/1993 | Singer et al. |
| 5,336,269 A | 8/1994 | Smits |
| 5,376,133 A | 12/1994 | Gramnas |
| 5,376,137 A | 12/1994 | Shorter et al. |
| 5,383,939 A | 1/1995 | James |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,484,389 A | 1/1996 | Stark et al. |
| 5,504,415 A | 4/1996 | Podrazhansky et al. |
| 5,545,232 A | 8/1996 | van de Veen |
| 5,545,233 A | 8/1996 | Fitzlaff |
| 5,571,205 A | 11/1996 | James |
| 5,571,212 A | 11/1996 | Cornelius |
| 5,571,213 A | 11/1996 | Allen |
| 5,586,557 A | 12/1996 | Nelson et al. |
| 5,650,704 A | 7/1997 | Pratt et al. |
| 5,656,915 A | 8/1997 | Eaves |
| 5,662,693 A | 9/1997 | Johnson et al. |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,746,774 A | 5/1998 | Kramer et al. |
| 5,749,668 A | 5/1998 | McIlvain et al. |
| 5,779,735 A | 7/1998 | Molino |
| 5,800,561 A | 9/1998 | Rodriguez |
| 5,800,568 A | 9/1998 | Atkinson et al. |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 5,910,720 A | 6/1999 | Williamson et al. |
| 5,919,149 A | 7/1999 | Allum |
| 5,955,667 A | 9/1999 | Fyfe |
| 5,957,981 A | 9/1999 | Gramnas |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| 6,061,577 A | 5/2000 | Andrieu et al. |
| 6,091,977 A | 7/2000 | Tarjan et al. |
| 6,113,642 A | 9/2000 | Petrofsky et al. |
| 6,129,766 A | 10/2000 | Johnson et al. |
| 6,165,226 A | 12/2000 | Wagner |
| 6,183,425 B1 | 2/2001 | Whalen et al. |
| 6,187,051 B1 | 2/2001 | van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,361,570 B1 | 3/2002 | Gow |
| 6,373,152 B1 | 4/2002 | Wang et al. |
| 6,409,695 B1 | 6/2002 | Connelly |
| 6,423,098 B1 | 7/2002 | Biedermann |
| 6,425,925 B1 | 7/2002 | Grundel |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,602,295 B1 | 8/2003 | Doddroe et al. |
| 6,610,101 B2 | 8/2003 | Herr et al. |
| 6,663,673 B2 | 12/2003 | Christensen |
| 6,671,531 B2 | 12/2003 | Al-Ali et al. |
| 6,719,806 B1 | 4/2004 | Zahedi et al. |
| 6,740,123 B2 | 5/2004 | Davalli et al. |
| 6,743,260 B2 | 6/2004 | Townsend et al. |
| 6,755,870 B1 | 6/2004 | Biedermann et al. |
| 6,764,520 B2 | 7/2004 | Deffenbaugh et al. |
| 6,770,045 B2 | 8/2004 | Naft et al. |
| 6,855,170 B2 | 2/2005 | Gramnas |
| 6,876,135 B2 | 4/2005 | Pelrine |
| 6,955,692 B2 | 10/2005 | Grundei |
| 6,966,882 B2 * | 11/2005 | Horst ................. 601/5 |
| 6,966,933 B2 | 11/2005 | Christensen |
| 7,029,500 B2 | 4/2006 | Martin |
| 7,063,727 B2 | 6/2006 | Van Phillips et al. |
| 7,118,601 B2 | 10/2006 | Yasui et al. |
| 7,131,998 B2 | 11/2006 | Pasolini |
| 7,137,998 B2 | 11/2006 | Bedard et al. |
| 7,147,667 B2 | 12/2006 | Bedard |
| 7,164,967 B2 | 1/2007 | Etienne-Cummings et al. |
| 7,295,892 B2 | 11/2007 | Herr et al. |
| 7,313,463 B2 | 12/2007 | Herr et al. |
| 7,367,958 B2 | 5/2008 | McBean et al. |
| 7,396,337 B2 | 7/2008 | McBean et al. |
| 7,410,338 B2 | 8/2008 | Schiele et al. |
| 7,431,737 B2 | 10/2008 | Ragnarsdottir et al. |
| 7,637,959 B2 | 12/2009 | Clausen et al. |
| 2002/0087216 A1 | 7/2002 | Atkinson et al. |
| 2002/0183803 A1 | 12/2002 | Fang et al. |
| 2002/0198604 A1 | 12/2002 | Schulman et al. |
| 2003/0029247 A1 | 2/2003 | Biedermann |
| 2003/0120353 A1 | 6/2003 | Christensen |
| 2003/0223844 A1 | 12/2003 | Schiele et al. |
| 2004/0044417 A1 | 3/2004 | Gramnas |
| 2004/0049290 A1 | 3/2004 | Bedard |
| 2004/0064195 A1 | 4/2004 | Herr |
| 2004/0088057 A1 | 5/2004 | Bedard |
| 2004/0102723 A1 | 5/2004 | Horst |
| 2004/0111163 A1 | 6/2004 | Bedard et al. |
| 2004/0181289 A1 | 9/2004 | Bedard et al. |
| 2004/0193286 A1 | 9/2004 | Grundei |
| 2004/0263127 A1 | 12/2004 | Turner et al. |
| 2005/0004495 A1 | 1/2005 | Goswami |
| 2005/0010139 A1 | 1/2005 | Aminian et al. |
| 2005/0070834 A1 | 3/2005 | Herr et al. |
| 2005/0107889 A1 | 5/2005 | Bedard et al. |
| 2005/0119763 A1 | 6/2005 | Christensen |
| 2005/0143838 A1 | 6/2005 | Collier |
| 2005/0197717 A1 | 9/2005 | Ragnarsdottir et al. |
| 2005/0283257 A1 | 12/2005 | Bisbee et al. |
| 2006/0041321 A1 | 2/2006 | Christensen |
| 2006/0064195 A1 | 3/2006 | Kern et al. |
| 2006/0069336 A1 | 3/2006 | Krebs et al. |
| 2006/0069448 A1 | 3/2006 | Yasui |
| 2006/0122710 A1 | 6/2006 | Bedard |
| 2006/0122711 A1 | 6/2006 | Bedard et al. |

| | | | |
|---|---|---|---|
| 2006/0135883 A1 | 6/2006 | Jónsson et al. | |
| 2006/0136072 A1 | 6/2006 | Bisbee et al. | |
| 2006/0155385 A1 | 7/2006 | Martin | |
| 2006/0224247 A1 | 10/2006 | Clausen et al. | |
| 2006/0235544 A1 | 10/2006 | Iversen et al. | |
| 2006/0249315 A1 | 11/2006 | Herr et al. | |
| 2007/0027555 A1 | 2/2007 | Palmer et al. | |
| 2007/0027557 A1 | 2/2007 | Jonsson | |
| 2007/0043449 A1 | 2/2007 | Herr et al. | |
| 2007/0050045 A1 | 3/2007 | Clausen et al. | |
| 2007/0123997 A1 | 5/2007 | Herr et al. | |
| 2007/0156252 A1 | 7/2007 | Jonsson et al. | |
| 2007/0162152 A1 | 7/2007 | Herr et al. | |
| 2010/0241242 A1 | 9/2010 | Herr et al. | |
| 2010/0312363 A1 | 12/2010 | Herr et al. | |
| 2010/0324699 A1 | 12/2010 | Herr et al. | |
| 2011/0040216 A1 | 2/2011 | Herr et al. | |

FOREIGN PATENT DOCUMENTS

| | | |
|---|---|---|
| DE | 3028608 | 2/1982 |
| DE | 42 29 330 | 3/1994 |
| DE | 195 21 464 A1 | 6/1995 |
| DE | 197 54 690 A | 7/1999 |
| DE | 201 17 080 U1 | 1/2002 |
| EP | 0 549 855 A2 | 9/1992 |
| EP | 0 549 855 A2 | 7/1993 |
| EP | 0 628 296 A2 | 12/1994 |
| EP | 0 718 951 A | 6/1996 |
| EP | 0 902 547 A | 3/1999 |
| EP | 1 066 793 | 1/2001 |
| EP | 1 107 420 A | 6/2001 |
| EP | 1 166 726 A1 | 1/2002 |
| EP | 1 169 982 A1 | 1/2002 |
| EP | 1 340 478 | 9/2003 |
| FR | 2623086 | 5/1989 |
| GB | 2149004 | 6/1985 |
| GB | 2201260 | 8/1988 |
| GB | 2 244 006 A | 11/1991 |
| GB | 2 260 495 A | 4/1993 |
| GB | 2 301 776 A | 12/1996 |
| GB | 2 302 949 A | 2/1997 |
| GB | 2 328 160 A | 2/1999 |
| GB | 2 334 891 A | 8/1999 |
| GB | 2 338 653 A | 12/1999 |
| GB | 2 367 753 A | 4/2002 |
| JP | 11056885 | 3/1999 |
| JP | 11000345 A2 | 6/1999 |
| JP | 20011277175 | 10/2001 |
| JP | 2002-191654 A | 7/2002 |
| SU | 1447366 | 12/1988 |
| WO | WO 93/24080 A1 | 12/1993 |
| WO | WO 94/06374 A1 | 3/1994 |
| WO | WO 95/26171 A1 | 10/1995 |
| WO | WO 96/41598 | 12/1996 |
| WO | WO 96/41599 | 12/1996 |
| WO | WO 97/00661 A | 1/1997 |
| WO | WO 98/25552 | 6/1998 |
| WO | WO 98/38951 A1 | 9/1998 |
| WO | WO 99/05991 A2 | 2/1999 |
| WO | WO 99/08621 A2 | 2/1999 |
| WO | WO 99/29272 | 6/1999 |
| WO | WO 00/27318 | 5/2000 |
| WO | WO 00/30572 A1 | 6/2000 |
| WO | WO 00/38599 A1 | 7/2000 |
| WO | WO 00/71061 | 11/2000 |
| WO | WO 01/17466 A2 | 3/2001 |
| WO | WO 01/50986 A1 | 7/2001 |
| WO | WO 01/72245 A2 | 10/2001 |
| WO | WO 03/003953 | 1/2003 |
| WO | WO 03/086245 A2 | 10/2003 |
| WO | WO 03/088373 A | 10/2003 |
| WO | WO 2004/017871 | 3/2004 |
| WO | WO 2004/017872 | 3/2004 |
| WO | WO 2004/017873 A1 | 3/2004 |
| WO | WO 2005/041819 A2 | 5/2005 |
| WO | WO 2005/048887 | 6/2005 |
| WO | WO 2005/079712 A | 9/2005 |

OTHER PUBLICATIONS

Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.

Copes/Bionic Ankle, The Most Significant Development in Ankle Prosthetics in Over a Half Century, 1985, 3 pages. USA.

Dietl, H. Bargehr, Der Einsatz von Elektronik bei Prothesen zur Versorgung der unteren Extremitat, Med. Orth. Tech. 117 1997, pp. 31-35.

Flowers, et al., "An Electrohydraulic Knee-Torque Controller for a Prosthesis Stimulator", Journal of Biomechanical Engineering: Transactions of the ASME; Feb. 1977, pp. 3-8.

Proteor, Assembly and Adjustment Instructions for 1P50-R, pp. 1-21, Sep. 2004.

Suga, T., et al., "Newly designed computer controlled knee-ankle-foot orthosis (Intellegent Orthosis)", Prostetics and Orthotics International, 1998, 22, 230-239.

Townsend M A et al., "Biomechanics and modeling of bipedal climbing and descending." Journal of Biomechanics 1976, vol. 9, No. 4, pp. 227-239, XP008078405.

Otto Bock, "The Electronic C-Leg® Knee Joint System, Instructions for Use", 2002, 30 pages, Germany.

International Search Report and Written Opinion; International Appl. No. PCT/US2006/004025, mailed Nov. 22, 2006, 12 pages.

Office Action in Chinese Application No. 200680010472.9, mailed on Feb. 27, 2009.

U.S. Appl. No. 12/157,727, filed Jun. 12, 2008, Herr.

* cited by examiner

FIG. 7

PROSTHETIC AND ORTHOTIC SYSTEMS USABLE FOR REHABILITATION

RELATED APPLICATIONS

The present application claims the benefit of priority under 35 U.S.C.§119(e) of U.S. Provisional Patent Application No. 60/649,417, filed on Feb. 2, 2005, entitled "PROSTHETIC AND ORTHOTIC SYSTEMS USABLE FOR REHABILITATION," and U.S. Provisional Patent Application No. 60/721,622 filed on Sep. 29, 2005, entitled "PROSTHETIC AND ORTHOTIC SYSTEMS USABLE FOR REHABILITATION," the entirety of each of which is hereby incorporated herein by reference and is to be considered a part of this specification.

BACKGROUND OF THE INVENTION

1. Field of the Invention

Embodiments of the invention relate to systems and methods for rehabilitation and, in particular, to powered prosthetic or orthotic systems usable to rehabilitate and/or train a patient.

2. Description of the Related Art

The number of disabled persons and amputees is increasing each year as the average age of individuals increases, as does the prevalence of debilitating diseases such as diabetes. As a result, the need for prosthetic and orthotic devices is also increasing. Conventional orthoses are often external apparatuses used to support a joint, such as an ankle or a knee, of an individual, and movement of the orthosis is generally based solely on the energy expenditure of the user. Many conventional prostheses, which include artificial substitutes for a missing limb, are also passive devices that rely mostly on the muscle strength of the user. Such passive devices can often lead to movement instability, high energy expenditure on the part of the disabled person or amputee, gait deviations and other short- and long-term negative effects.

To address some of the foregoing drawbacks, some prosthetic and orthotic devices are equipped with basic controllers that artificially mobilize joints and are capable of powering basic motions. Certain users, such as first-time users, however, often may have difficulty adapting to the powered motion of such prosthetic or orthotic devices due to a lack of experience, voluntary muscle control and/or balance.

SUMMARY OF THE INVENTION

In view of the foregoing, a need exists for a powered rehabilitation device that is adaptable to the needs and/or abilities of a user, such as a rehabilitation device adaptable to replace or assist a variable amount of muscle function of a user. There is also a need for improved methods of training and rehabilitation using a powered rehabilitation device in place of, or in combination with, a passive prosthetic device.

In certain embodiments, a method for rehabilitation is disclosed that includes providing a patient with a rehabilitation device that is attachable to a limb of the patient and has an actively actuatable joint assembly. The method further includes selecting a first power level of the rehabilitation device, wherein the first power level is less than a maximum level of the rehabilitation device such that the patient, when moving, is partially assisted by the rehabilitation device while using his or her own muscles. The method also includes selecting, after a length of time, a second power level of the rehabilitation device, wherein the second power level is higher than the first power level and at least partially replaces muscle function of the patient, when moving, compared to the first power level.

In certain further embodiments, the aforementioned method additionally includes selecting a third power level of the rehabilitation device, wherein selecting the first power level corresponds to a first rehabilitation-oriented action and selecting the third power level corresponds to a second rehabilitation-oriented action different than the first rehabilitation-oriented action. The method may also include determining a sensitivity level of the rehabilitation device.

In certain embodiments, a training device is disclosed for use with a limb of a patient. For example, the training device may comprise an actively actuatable joint, an interface module and a control module. The interface module may be configured to receive a selection of at least one of a plurality of power settings associated with one or more motions of the actively actuatable joint. The control module may be configured to output at least one control signal, based at least on the selection of the at least one power setting, indicative of a power of the actively actuatable joint for at least partially replacing muscle function of the patient during a first category of motion of the training device.

In certain further embodiments, the power of the actively actuatable joint corresponds to a propulsion of the actively actuatable joint, such as, for example, a prosthetic knee joint. In other embodiments, the actively actuatable joint may comprise other types of prosthetic joints or an orthotic joint.

In other embodiments, a method of training a patient is disclosed. The method comprises providing a patient with a training device having a powered actuatable joint and being configured to attach to a limb of the patient, wherein the training device is provided temporarily to train the patient to use a second prosthetic device. The method further includes selecting a first power level of the training device corresponding to a first rehabilitation-oriented action and selecting a second power level of the training device corresponding to a second rehabilitation-oriented action different than the first rehabilitation oriented action. In certain embodiments, the selecting of the first and second power levels is based on a training level of the patient, wherein the first and second power levels are, respectively, less than a first maximum power level and a second maximum power level.

In certain embodiments, a powered lower-limb prosthesis is disclosed that has propulsive capabilities. The prosthesis includes an actively actuatable knee joint, a user interface module and an adjustable-power module. The user interface module may be configured to receive a selection of at least one of a plurality of power settings. The adjustable-power module may be configured to output one or more control signals for controlling an amount of power to be applied during a movement of the actively actuatable knee joint, wherein the one or more control signals is based at least in part on the selection of the at least one power setting.

In certain embodiments, a method of training an amputee is disclosed. The method includes using a first prosthetic device to perform a first motion by an amputee such that movement of the first prosthetic device is caused by a first muscle power of the amputee. The method also includes replacing the first prosthetic device with a second powered prosthetic device and using the second powered prosthetic device to perform the first motion by the amputee such that movement of the second powered prosthetic device is caused by a second muscle power of the amputee, wherein the second muscle power is less than the first muscle power. In addition, the method includes replacing, after using the second powered prosthetic device, the second powered prosthetic device with the first prosthetic device. In certain embodiments, the first prosthetic device is a passive prosthetic device.

Certain embodiments of the invention include a powered rehabilitation system that comprises a device associated with a limb, such as a prosthetic or orthotic device, and an adjustable-power module. The adjustable-power module is capable of selectively powering active movement of the rehabilitation device at a plurality of different power levels. For example, the power level of the rehabilitation device may be adjusted to accommodate particular needs and/or abilities of a user.

Another embodiment of the invention includes a method for rehabilitation of a patient. The method comprises selectively adjusting the power provided to a rehabilitation device, such as a prosthetic or an orthotic device, based on particular needs and/or abilities of the patient. Such selective adjusting may comprise assigning particular power levels for the rehabilitation device to each of a plurality of rehabilitation-oriented actions. The method may also include selecting an appropriate sensitivity level of the rehabilitation device that determines an ease of initiation of certain rehabilitation-oriented functions of the rehabilitation device.

Certain embodiments of the invention include a machine loadable software program for a processor for controlling the movement of a rehabilitation device associated with a limb. The software program includes a power module and an interface module, which may further include a control module. The interface module receives input from a user relating to the desired operation of the rehabilitation device. For example, the interface module may receive input indicative of a particular power level and/or sensitivity level for a particular rehabilitation-oriented action. The control module determines the appropriate power level and/or adjustments to be made to the rehabilitation device based on the user input and/or the current power level of the rehabilitation device. The control module then outputs a control signal to an actuatable joint of the rehabilitation device based at least on the determination by the control module.

In certain embodiments, a rehabilitation device comprises a powered prosthetic knee device having propulsive capabilities that advantageously offer certain clinical benefits. For example, such clinical benefits may include, but are not limited to: improved kinematics (e.g., normalized pelvic obliquity, improved pelvic rotation), reduced energy consumption (e.g., oxygen consumption), restored dynamics (e.g., powered knee swing flexion/extension and powered stance extension), functional benefits for traumatic amputees, combinations of the same and the like. Furthermore, the rehabilitation device may be designed to provide powered knee flexion and/or extension according to the user's mobility needs, enabling the user to achieve a more natural gait.

For example, in certain embodiments, the rehabilitation device comprises a motorized prosthetic knee for trans-femoral amputees. A motorized actuator module may generate power according to the amputee's need to adequately execute different portions of locomotion. For instance, locomotion portions requiring specific power management may include, but are not limited to, one or more of the following: level ground walking, stair, incline ascent or descent, sitting down and standing up. In certain embodiments, the motorized knee unit substitutes the eccentric and concentric muscle-work generally required during these types of actions, providing for a more natural gait.

For purposes of summarizing the disclosure, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENTS

Embodiments of the invention disclosed herein relate generally to rehabilitating and/or training a patient. In certain embodiments, an adjustable-powered prosthetic or orthotic device is used to rehabilitate and/or train the limb of a user. For example, such a rehabilitation device may be used by amputees to increase their movement ability, agility, and/or performance. The adjustable power feature also allows the rehabilitation device to be used by a broader range of persons with varying types and/or degrees of disabilities.

Embodiments of the rehabilitation device provide a number of advantages to users and/or therapists. For example, the powered rehabilitation device may provide sufficient support and stability during different types of activity (e.g., normal walking, incline walking, ascending and descending stairs) of patients who otherwise may lack sufficient muscle power to ambulate unassisted.

While the following description sets forth various embodiment-specific details, it will be appreciated that the description is illustrative only and should not be construed in any way as limiting the disclosure. Furthermore, various applications of the invention, and modifications thereto, which may be recognized by a skilled artisan from the disclosure herein, are also encompassed by the general concepts described herein.

The terms "prosthetic" and "prosthesis" as used herein are broad terms and are used in their ordinary sense and refer to, without limitation, any system, device or apparatus that may be used as an artificial substitute or support for a body part.

The term "orthotic" and "orthosis" as used herein are broad terms and are used in their ordinary sense and refer to, without limitation, any system, device or apparatus that may be used to support, align, prevent, protect, correct deformities of, immobilize, or improve the function of parts of the body, such as joints and/or limbs.

The term "rehabilitation device" as used herein is a broad term and is used in its ordinary sense and refers to, without limitation, any system, device or apparatus used for the reconditioning or training of a patient. For example, a rehabilitation device may include a prosthetic or orthotic device usable for rehabilitation. In certain embodiments, the rehabilitation device may include a device usable for training a patient that has lost a portion of a limb (e.g., due to amputation) to assist the patient in regaining mobility.

The terms "rehabilitation-oriented action" and "rehabilitation-oriented function" as used herein are broad terms and each is used in its ordinary sense and includes, without limitation, a particular movement or category of movements generally performed by a healthy limb and/or a rehabilitation device associated with a limb. For example, a rehabilitation-oriented action or function for a lower limb may include at least one of the following: level ground walking, ascending/descending stairs and/or inclines, sitting, standing, running or the like.

The term "power" as used herein with respect to a rehabilitation device is a broad term and is used in its ordinary sense and refers to, without limitation, a propulsion force and/or other active movement of the rehabilitation device. For example, the power of the rehabilitation device may relate to the amount of motorized force needed by the rehabilitation device to replace or assist the functioning of remaining muscles of the user during locomotion. For instance, the rehabilitation device may perform at least one of the following: active limb (e.g., leg) swing initiation, bending and/or straightening of a limb, advancement of the limb from a trailing position, and initiation of desirable hip rotation during limb swing to transfer the load to the other limb.

The term "sensitivity" as used herein with respect to a rehabilitation device is a broad term and is used in its ordinary sense and refers to, without limitation, a level of user difficulty associated with initiating one or more rehabilitation-oriented functions of the rehabilitation device. In certain embodiments, a sensitivity level corresponds to an effort and/or skill needed by the patient to initiate a desired rehabilitation-oriented action. For example, a low sensitivity level may be associated with a narrow range of sensed angle, pressure, and/or acceleration measurements that a user attains to trigger a particular rehabilitation-oriented function, while a high sensitivity level may be associated with a broad range of angle, pressure, and/or acceleration measurements that are capable of triggering the particular rehabilitation-oriented function.

The term "passive" as used herein with respect to a prosthetic device, orthotic device, rehabilitation device, or the like, is a broad term and is used in its ordinary sense, and refers to, without limitation, a device that does not actively adjust movement and/or a position of the device. For instance, a passive device may rely upon the muscle power of the user for substantially all of the movement of the device and/or may regulate a resistance of a joint assembly of the device. Furthermore, a "passive mode" of a powered device may refer to a state of the device in which movement and/or a position of the device is caused wholly by muscle power of the user.

The features of the system and method will now be described with reference to the drawings summarized above. Throughout the drawings, reference numbers are reused to indicate correspondence between referenced elements. The drawings, associated descriptions, and specific implementation are provided to illustrate embodiments of the invention and not to limit the scope of the disclosure.

Moreover, methods and functions described herein are not limited to any particular sequence, and the acts or blocks relating thereto can be performed in other sequences that are appropriate. For example, described acts or blocks may be performed in an order other than that specifically disclosed, or multiple acts or blocks may be combined in a single act or block.

Figure 1:
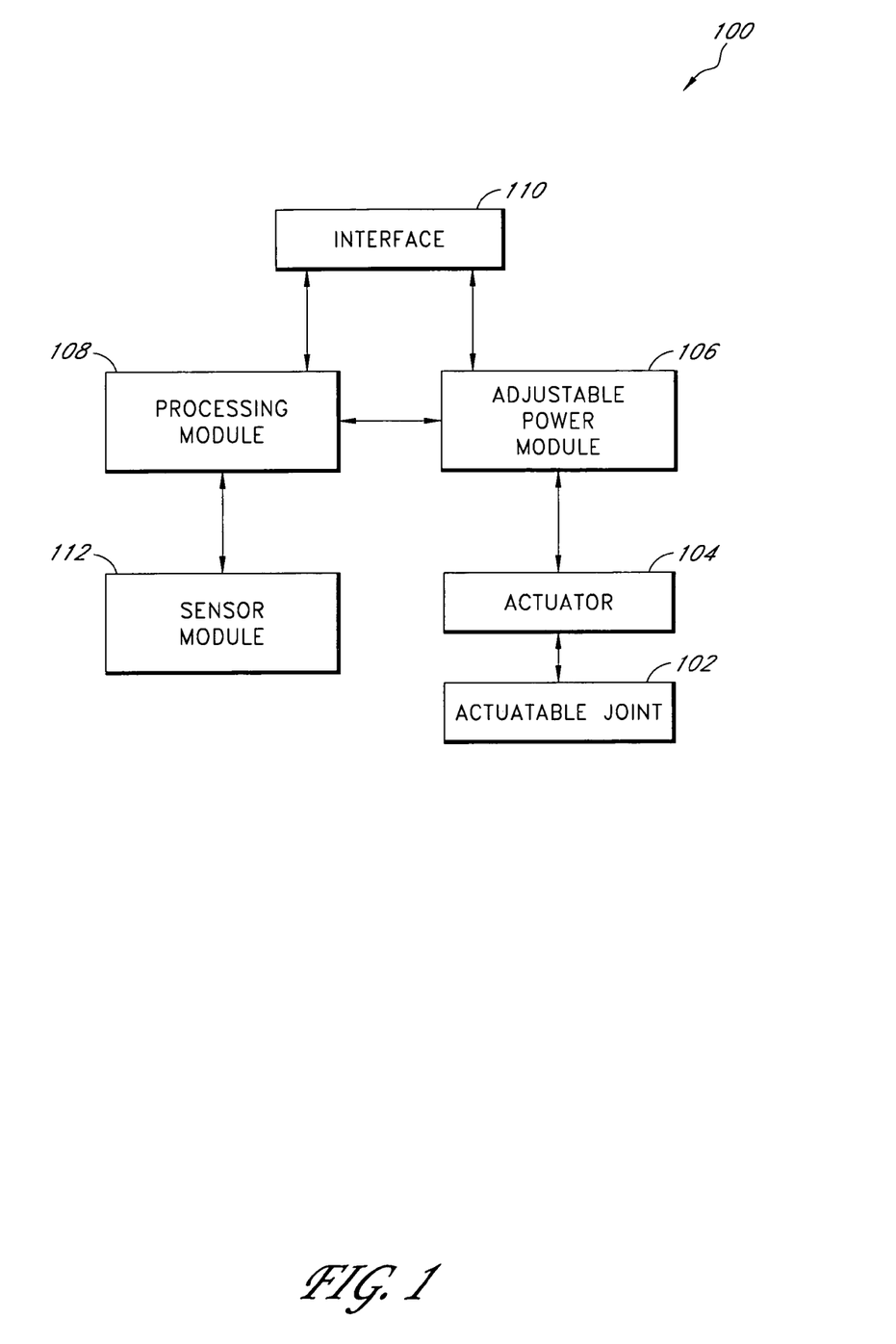
FIG. 1 illustrates a block diagram of a control system for a rehabilitation device according to certain embodiments of the invention.

FIG. 1 illustrates a block diagram of a control system 100 for a rehabilitation device according to certain embodiments of the invention. In particular, the control system 100 is usable with an actively controlled or articulated rehabilitation device, such as a prosthetic or an orthotic device, that is associated with the movement of a limb of a user. In certain embodiments, the rehabilitation device is advantageously adapted to mimic and/or facilitate natural movement of a human joint.

As shown, the control system 100 includes an actuatable joint 102 that is actively controlled by an actuator 104. In certain embodiments, the actuatable joint 102 corresponds to a lower limb joint, such as an ankle or a knee. The actuator 104 may comprise a wide variety of actuating mechanisms that are configured to actively adjust the actuatable joint 102, such as, for example, by adjusting an angle between limb portions attached at the actuatable joint 102. For instance, in certain embodiments, the actuator 104 may comprise a linear actuator, a rotatable mechanism, a movable post or the like, controlled by a motorized module to adjust an angle between two limb portions.

The control system 100 further includes an adjustable-power module 106 advantageously capable of adjusting the power supplied by the actuator 104 to the actuatable joint 102. In certain embodiments, the adjustable-power module 106 outputs one or more control signals for adjusting the actuator 104.

In certain embodiments, the adjustable-power module 106 includes a plurality of power levels and/or rehabilitation settings that allow the functioning of the rehabilitation device to be adapted to the particular needs and/or abilities of the user. In certain embodiments, the power levels correspond to amounts of user muscle function or muscle power, of the user's remaining muscles, replaced and/or assisted by the motorized movement of the rehabilitation device during motion by the user.

For instance, the power of the rehabilitation device may be set at a lower level (e.g., 10% of the total power) for a first-time user who has previous experience with a passive prosthetic device. At this lower level, the rehabilitation device replaces and/or assists a relatively low amount of user muscle function or muscle power with respect to the actual activity level of the patient and allowing for slow and gradual adaptation to the powered rehabilitation device. That is, during initial training, the user is able to use the prosthesis in a similar way as the passive prosthesis he or she was used to. A more advanced user, on the other hand, may operate the rehabilitation device at a higher power level (e.g., 90% of the total power), wherein the rehabilitation device replaces and/or assists a larger amount of user muscle function or muscle power, thus relying more on the user's ability to use the power of the rehabilitation device to his or her advantage. Similar power adjustments may also be made based on the severity of the user's disability. Thus, the adjustable power function may be used to assist a user to regain natural or normal gait dynamics.

In certain embodiments, the adjustable power module 106 may include a control drive module used to translate high-level plans or instructions received from a processing module 108 into low-level control signals to be sent to the actuator 104. For example, the adjustable-power module 106 may comprise a printed circuit board that implements control algorithms and tasks related to the management of the actuator 104. In addition, the control drive module may be used to implement a hardware abstraction layer that translates the decision processes of the processing module 108 to the actual hardware definition of the actuator 104. In other embodiments, the control drive module may provide feedback to the processing module 108 regarding the position or movement of the actuator 104 or actuatable joint 102.

In certain embodiments of the invention, the adjustable power module 106 is located within the rehabilitation device. In other embodiments, the adjustable power module 106 may be located on the outside of the rehabilitation device, such as on a socket, or remote to the rehabilitation device.

The illustrated adjustable-power module 106 receives inputs from the processing module 108 and an interface 110. The processing module 108 advantageously processes data received from the other components of the control system 100. In certain embodiments, the processing module 108 includes a plurality of sub-modules that comprise logic embodied in hardware or firmware or that comprise a collection of software instructions. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

In certain embodiments, the processing module 108 includes a printed circuit board that is positioned on the rehabilitation device. For example, at least a portion of the processing module 108 and at least a portion of the adjustable-power module 106 may be located on the same printed circuit board. In other embodiments, at least a portion of the processing module 108 may be remote to the rehabilitation device. In such embodiments, the processing module 108 may communicate with other portions of the control system 100 through wired and/or wireless transmissions.

In certain embodiments, the processing module 108 may also be configured to receive through the interface module 110 user- or activity-specific instructions from a user or from an external device. The processing module 108 may also receive updates to already existing instructions. Furthermore, the processing module 108 may communicate with a personal computer, a laptop, a portable computing device, a personal digital assistant, a remote control device, a cellular phone or the like, to download or receive operating instructions. Activity-specific instructions may include, for example, data relating to rehabilitation-oriented actions performable by the rehabilitation device.

The illustrated interface 110 advantageously receives input, such as user input, relating to the desired operation of the rehabilitation device. For example, the interface 110, which may be implemented in whole or in part in software, may allow for individual fine-tuning of the function of the rehabilitation device during different portions of locomotion. For instance, the user interface may receive input indicative of a particular power level and/or sensitivity level for a particular rehabilitation-oriented action. The interface 110 provides this input to the processing module 108 and/or the adjustable-power module 106, which determine(s) the appropriate power level and/or adjustments to be made to the actuator 104 based on the user input and/or the current power level of the rehabilitation device.

In certain embodiments, the interface 110 comprises a device that the user accesses to control or manage portions or functions of the rehabilitation device. For example, the interface 110 may include a flexible keypad having multiple buttons or a touch screen usable to receive information from a user. In other embodiments, the interface 110 may comprise a machine-executable software program that a user and/or therapist may access to adjust the rehabilitation device. Such a software program may advantageously be run on a processor, such as a personal computer, that is remote to the rehabilitation device.

The interface 110 may also comprise means for conveying and/or displaying information to a user. For instance, the interface 110 may comprise one or more light emitting diodes (LEDs), a graphical user interface, an audible alarm, a vibrator, combinations of the same or the like, that allow a user to send instructions to or receive information from the control system 100. The interface 110 may also be advantageously located on the rehabilitation device and/or may comprise a USB connector, an RS 232 connector or the like usable for communication to an external computing device.

In a further embodiment, the interface 110 comprises an input that switches the rehabilitation device between active and passive modes. For instance, during an active mode, the adjustable-power module 106 actively controls the movement of the rehabilitation device (e.g., the actuatable joint 102). While in the passive mode, the rehabilitation device advantageously operates in a free-swing mode that allows for free movement of the actuatable joint 102 and relies upon muscle power of the user for movement.

The control system 100 further includes a sensor module 112. In certain embodiments, the rehabilitation device is controlled, at least in part, based on sensory data collected from a healthy (sound) limb of a user. For instance, sensory data may include information related to the positioning and/or loading of the healthy limb, which information may be wirelessly relayed to the processing module 108 to result in one or more predefined actions of the rehabilitation device. Examples of such sensory control, as used with a motion-controlled prosthetic foot, are described in more detail in the following applications, each of which is hereby incorporated herein by reference in its entirety to be considered part of this specification: U.S. patent application Ser. No. 11/056,344, filed Feb. 11, 2005, published as U.S. Patent Application Publication No. 2005/0197717 A1; U.S. patent application Ser. No. 11/218,923, filed on Sep. 1, 2005; and U.S. patent application Ser. No. 11/315,648, filed Dec. 22, 2005.

In certain embodiments, the sensor module 112 is associated with a lower-limb rehabilitation device and is attached to the lower leg (e.g., the shin) of the healthy leg of an amputee. The processing module 108 receives data from the sensor module 112 and adjusts the rehabilitation device to imitate the motion pattern of the healthy leg. In certain embodiments, such imitation is performed substantially in real time. In such an embodiment, it may be preferable that when operating on an incline or a decline, the first step of the user be taken with the healthy leg. Such would allow measurements taken from the natural movement of the healthy leg prior to adjusting the rehabilitation device. For example, the sensor module 112 may read data (e.g., motion, load and/or position data) from the healthy limb at a rate of approximately 1.3 kHz. In yet other embodiments, the sensor module 112 comprises a plurality of pressure sensors in an insole of the healthy leg and a processor located on the lower leg that is in communication with the plurality of sensors.

In certain embodiments, the sensor module 112 is used to measure variables relating to the rehabilitation device, such as the position and/or the movement of the rehabilitation device. In such an embodiment the sensor module 112 is advantageously located on the rehabilitation device. For example, the sensor module 112 may be located near a mechanical center of rotation of the actuatable joint 102 of the rehabilitation device. In other embodiments, the sensor module 112 may be located on the user's natural limb, such as a stump of an amputee, that is attached to, or associated with, the rehabilitation device. In such embodiments, the sensor module 112 captures information relating to the movement of the natural limb on the user's rehabilitation-device side to adjust the rehabilitation device.

In certain embodiments, the sensor module 112 advantageously includes a plurality of sensors, such as accelerometers, positioned at different locations on the rehabilitation device. For example, the sensor module 112 may comprise three accelerometers that measure acceleration of the rehabilitation device in three substantially, mutually perpendicular axes.

In other embodiments, the sensor module 112 may include one or more other types of sensors in combination with, or in place of, accelerometers. For example, the sensor module 112 may include a gyroscope configured to measure the angular speed of body segments and/or the rehabilitation device. In other embodiments, the sensor module 112 includes a plantar pressure sensor configured to measure, for example, the vertical plantar pressure of a specific underfoot area. In yet other embodiments, the sensor module 112 may include one or more of the following: kinematic sensors, single-axis gyroscopes, single- or multi-axis accelerometers, load sensors, flex sensors or myoelectric sensors that may be configured to capture data from the rehabilitation device and/or the user's healthy limb.

In certain embodiments, the sensor module 112 and/or processor 108 are further configured to detect gait patterns and/or events. For example, the sensor module 112 may determine whether the user is in a standing or stopped position, is walking on level ground, is ascending or descending stairs or sloped surfaces, or the like.

Although the control system 100 has been described with reference to particular arrangements, a wide variety of alternative configurations of the control system may be used with embodiments of the invention. For example, the control system 100 may further include a memory that is remote to or associated with the processing module 108 (e.g., a cache). Such a memory may store one or more of the following types of data or instructions: an error log for the other components of the control system 100; information regarding gait patterns or curves; information regarding past activity of the user (e.g., number of steps); control parameters and set points; information regarding software debugging or upgrading; preprogrammed algorithms for basic movements of the prosthetic or orthotic system; calibration values and parameters relating to the sensor module 112 or other components; instructions downloaded from an external device; combinations of the same or the like. Moreover, the memory may comprise any buffer, computing device, or system capable of storing computer instructions and/or data for access by another computing device or a computer processor. The memory may comprise a random access memory (RAM) or may comprise other integrated and accessible memory devices, such as, for example, read-only memory (ROM), programmable ROM (PROM), and electrically erasable programmable ROM (EEPROM). In another embodiment, the memory comprises a removable memory, such as a memory card, a removable drive, or the like.

It is also contemplated that the components of the control system 100 may be integrated in different forms. For example, the components may be separated into several sub-components or may be separated into devices that reside at different locations and that communicate with each other, such as through a wired and/or wireless network. For example, in certain embodiments, the modules may communicate through RS232 or serial peripheral interface (SPI) channels. Multiple components may also be combined into a single component. It is also contemplated that the components described herein may be integrated into a fewer number of modules.

In certain embodiments, the rehabilitation device is controlled, at least in part, by an electronic device that executes a portion of, or communicates with, the control system 100. For example, the electronic device may comprise a computer system, a personal computer, a laptop, a personal digital assistant (PDA), a handheld device, a cellular phone, or the like for executing software that controls functions of the rehabilitation device. Such an electronic device may communicate with the rehabilitation device through wired and/or wireless communications (e.g., radio frequency, Bluetooth, infrared, or the like).

Figure 2:
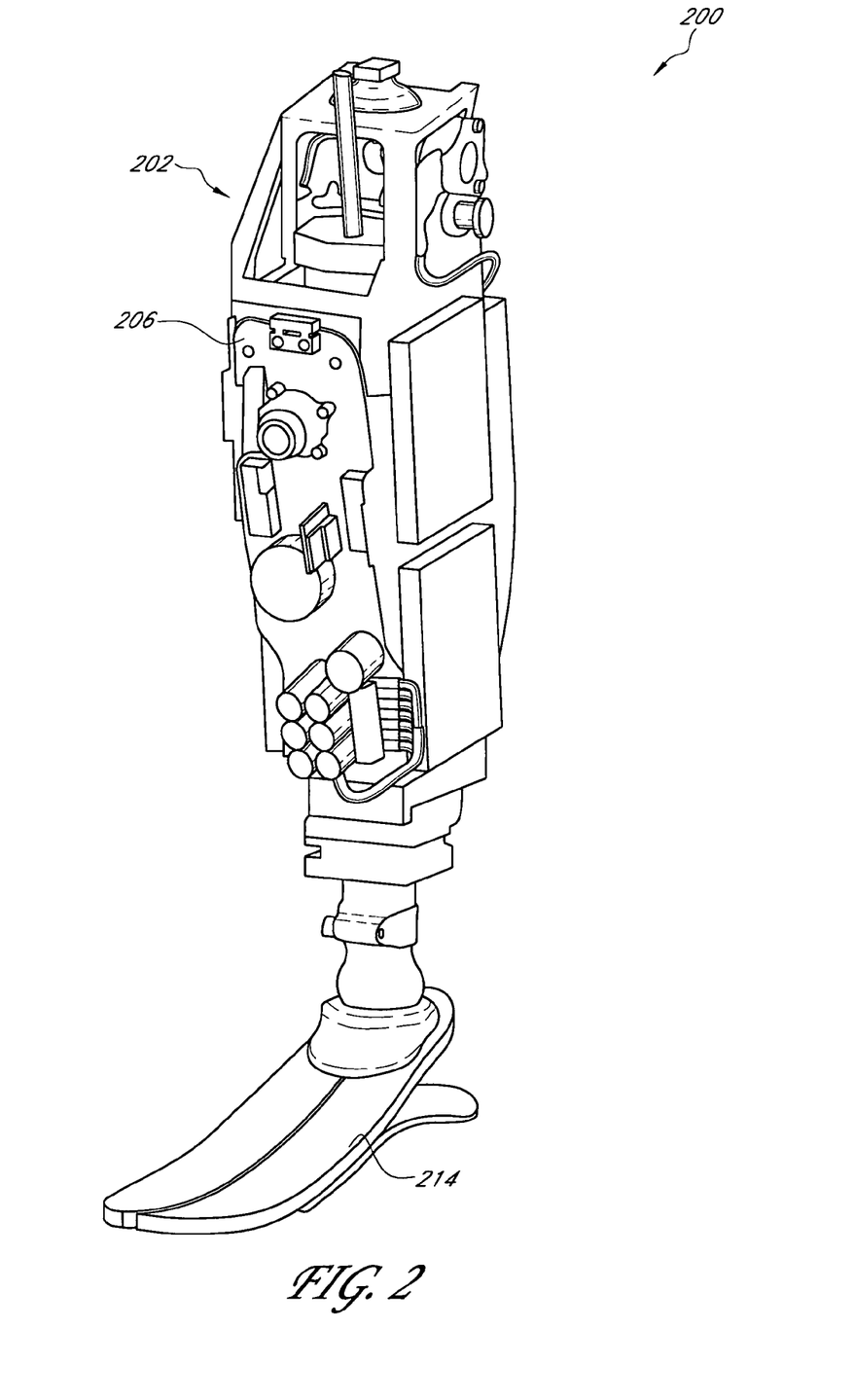
FIG. 2 illustrates an exemplifying embodiment of a rehabilitation device that may use the control system of FIG. 1.

FIG. 2 illustrates a rehabilitation device 200 according to certain embodiments of the invention. In certain embodiments, the rehabilitation device 200 utilizes the control system 100 of FIG. 1 to actively control rehabilitation-oriented functions of the rehabilitation device 200. The illustrated rehabilitation device 200 advantageously attaches to a stump of a lower limb of an amputee and is usable to assist and/or replace power expended by the remaining muscles of the amputee (e.g., the upper leg muscles) to ambulate with the rehabilitation device.

As shown, the rehabilitation device 200 comprises a powered prosthetic knee joint usable to mimic normal movement of a healthy leg. For example, an electronic control system of the rehabilitation device 200 may adjust external propulsive capabilities of the rehabilitation device by controlling an actuatable knee joint 202. In certain embodiments, the actuatable knee joint 202 may include a motorized module that couples to a transtibial post connecting to a prosthetic foot 214. For example, the prosthetic foot 214 may include a configuration disclosed in U.S. patent application Ser. No. 10/642,125, filed Aug. 15, 2003, and published as U.S. Patent Application Publication No. 2005/0038524 A1, which is hereby incorporated herein by reference in its entirety to be considered a part of this specification.

For instance, in certain embodiments, an adjustable-power module 206 and/or a processing module may adapt the power of the actuatable knee joint 202 by executing a series of software instructions that take into account a height, weight, experience, and/or intended rehabilitation-oriented action of the user.

In certain embodiments, the rehabilitation device 200 comprises an active (or powered) mode and a free-swing mode. During the active mode, the adjustable-power module 206 actively controls movement of the actuatable knee joint 202, as discussed in more detail above. Such an active mode advantageously provides for an automatic movement of the rehabilitation device 200. In the passive mode, the rehabilitation device 200 operates in a free-swing mode that allows for free movement of the actuatable knee joint 202, as opposed to other powered prosthetic devices that become stiff when powered down. Such a passive mode advantageously allows a user to maintain a particular gait by using his or her own muscle strength (e.g., upper leg strength) and range of motion of his or her stump.

In certain embodiments, the rehabilitation device 200 further comprises a plurality of LEDs that indicate the status of operation of the rehabilitation device 200. For example, at least one LED may confirm the status of the communication between the rehabilitation device 200 and a corresponding sensor module. Audible alarms may also be used to indicate the battery level, the calibration status of the rehabilitation device 200, combinations of the same and the like.

In certain embodiments, the rehabilitation device 200 may further comprise a rubber socket cover that protects a socket of the device 200 and/or a front and rear hood that protects inner components of the rehabilitation device 200 (e.g., the adjustable-power module 206, an actuator, an input/output (I/O) module, processing module, and the like).

The rehabilitation device may also take on other lower-limb configurations, such as those described in the following patents and applications, each of which is hereby incorporated herein by reference in its entirety to be considered part of this specification: U.S. patent application Ser. No. 10/721,764, filed Nov. 25, 2003, and published as U.S. Patent Application Publication No. 2004/0181289 A1; U.S. patent application Ser. No. 10/627,503, filed Jul. 25, 2003, and published as U.S. Patent Application Publication No. 2004/0088057 A1; U.S. patent application Ser. No. 10/600,725, filed Jun. 20, 2003, and published as U.S. Patent Application Publication No. 2004/0049290 A1; U.S. patent application Ser. No. 11/123,870, filed on May 6, 2005; U.S. patent application Ser. No. 11/077,177, filed on Mar. 9, 2005, and published as U.S. Patent Application Publication No. 2005/0283257 A1; U.S. Pat. No. 6,610,101, issued on Aug. 26, 2003; and U.S. Pat. No. 6,764,520, issued Jul. 20, 2004.

In certain embodiments, the illustrated rehabilitation device 200 advantageously utilizes artificial intelligence that operates within high and low-level software layers to continuously observe the state of the respective human system interface. For example, the high-level code may be responsible for the management of biomechanical events and the amputee-device interaction, such as by calculating an appropriate power level needed to perform a particular rehabilitation-oriented function. The low-level code may manage the interaction between the rehabilitation device 200 and a respective instrumented foot having sensor components.

Figure 3:
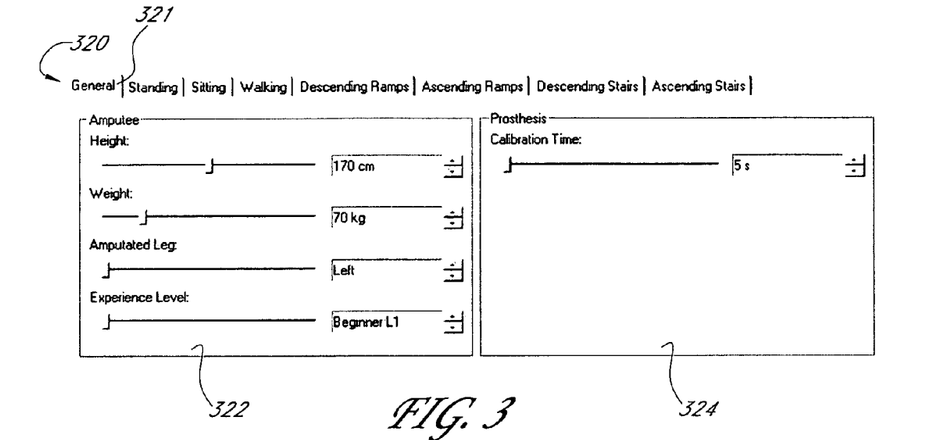
FIG. 3 illustrates an exemplifying embodiment of a first screen shot of a user interface for the control system of FIG. 1.

FIG. 3 illustrates an exemplifying embodiment of a screen display 300 of a user interface for receiving input relating to the control of a rehabilitation device, such as the rehabilitation device 200 of FIG. 2. In particular, the screen display 300 comprises a graphical user interface that may be used to gather data from a user, such as a patient or a therapist (e.g., a prosthetist or an orthotist), for controlling the rehabilitation device.

As shown, the screen display 300 includes a plurality of selectable tabs 320 that correspond to settings for a plurality of rehabilitation-oriented functions. For example, a user may select any of the tabs 320 to access and/or input information pertaining to the respective rehabilitation-oriented function of the rehabilitation device. As shown, the tabs 320 include a "General" tab 321 that activates user input widows for receiving physiological data of the user and/or configuration data of the rehabilitation device.

As illustrated, when the "General" tab 321 is selected, the screen display 300 includes an amputee window 322 for receiving physiological parameters relating to the user of the rehabilitation device. In particular, the amputee window 322 may receive information relating to the user's height, the user's weight, an identification of the amputated limb (e.g., left or right leg), and an experience level of the user. In other embodiments, the amputee window 322 may be configured to collect and/or display additional or less information as appropriate.

In certain embodiments, the parameters inputted through the amputee window 322 may be used to calculate a default power of the rehabilitation device. For instance, the experience level setting may be used to select between a variety of power levels that each correspond to a percentage of the maximum default power of the rehabilitation device. Such embodiments enable a user to fine-tune a power of the rehabilitation device according to the needs and/or abilities of the user. For example, a ten-level power system may include three beginner levels (e.g., Beginner L1, L2 and L3), four intermediate levels (e.g., Intermediate L1, L2, L3 and L4) and three advanced levels (Advanced L1, L2 and L3), wherein each of the levels corresponds to approximately ten percent of the maximum default power of the rehabilitation device. That is, as the user progresses in his or her ability to use the rehabilitation device, the power settings of the rehabilitation device may be increased to alleviate the amount of muscle power expended by the user. In yet other embodiments, the power setting(s) of the rehabilitation device may be selected to compensate for lost muscle function of the user.

The screen display 300 further includes a prosthesis window 324 that receives input relating to a calibration of the rehabilitation device. In particular, the prosthesis window 324 allows a user to set a calibration time for the rehabilitation device. For example, the calibration time may determine how long a user must use the rehabilitation device before the rehabilitation device will enter an active, or powered, mode. Such a calibration time may enable the rehabilitation device to gather and/or analyze data collected by a sensor module prior to active movement of the rehabilitation device.

Figure 4:
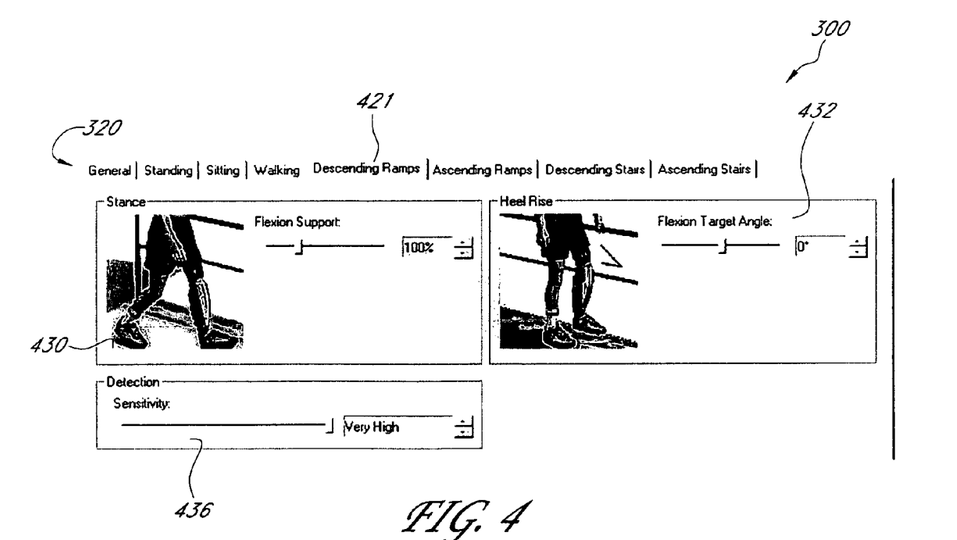
FIG. 4 illustrates an exemplifying embodiment of a second screen shot of a user interface for the control system of FIG. 1.

FIG. 4 illustrates the screen display 300 with a "Descending Ramps" tab 421 selected from the plurality of tabs 320. In certain embodiments, selecting the "Descending Ramps" tab 421 allows a user to access inputs and/or dialog boxes for adjusting parameters of the rehabilitation device relating to user movement while traveling down a ramp.

As illustrated, the screen display 300 includes a stance window 430, a heel rise window 432 and a detection window 436. The stance window 430 allows a user to adjust an amount of flexion support of the rehabilitation device. For instance, the adjustable flexion support value may correspond to how much resistance to bending the prosthetic knee is provided when a majority of the user's weight is shifted onto the rehabilitation device.

The heel rise window 432 allows a user to adjust a flexion target angle of the rehabilitation device. For instance, the flexion target angle may include a desired angle to which the prosthetic knee of the rehabilitation device will rise when the user shifts his or her weight to the corresponding healthy leg.

The detection window 436 allows a user to adjust a sensitivity of the rehabilitation device. In certain embodiments, the sensitivity scale determines the ease of the initiation of the rehabilitation-oriented actions by the rehabilitation device, as discussed in more detail above. For instance, a lower sensitivity level may indicate that more effort and/or skill is required from the user-amputee to initiate the desired action (e.g., descending a ramp) of the rehabilitation device. Thus, the sensitivity can be adjusted to the experience and/or ability of the user.

Although FIGS. 3 and 4 illustrate particular embodiments of the screen display 300, a variety of alternative configurations or types of displays may be used. For example, parameters for the plurality of rehabilitation-oriented functions may be input through menus accessible through hypertext links and/or on one or more web pages. In other embodiments, one or more settings may by input through an interface device attached to the rehabilitation device.

Figure 5:
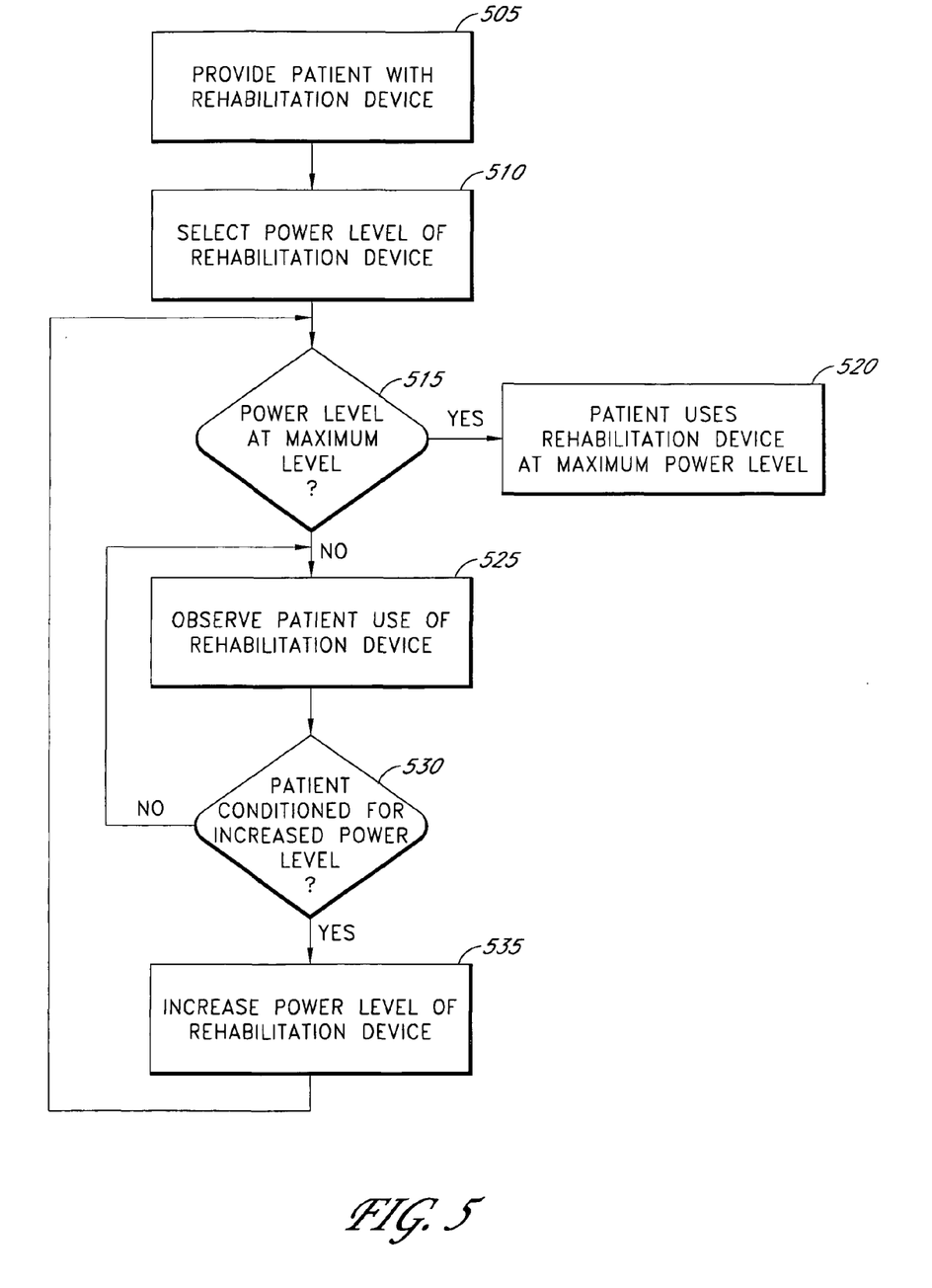
FIG. 5 illustrates an exemplifying embodiment of a flowchart of a rehabilitation process for conditioning a patient's use of a powered rehabilitation device.

FIG. 5 illustrates an exemplifying embodiment of a flowchart of a rehabilitation process 500 usable by a therapist and/or patient in connection with the use of a rehabilitation device, such as the rehabilitation device 200 of FIG. 2. In certain embodiments, the rehabilitation process 500 is performed in whole or in part during one or more visits between a patient and his or her therapist (e.g., prosthetist).

At the beginning of rehabilitation, a user often has difficulty performing various rehabilitation-oriented actions due to lack of skills, voluntary control and/or body balance. The rehabilitation process 500 described herein advantageously facilitates the user's progress in restoring symmetry, balance and/or power to user movement, such as, for example, a gait of the user.

The rehabilitation process 500 begins with Block 505 wherein the therapist provides a patient with a rehabilitation device. In certain embodiments, the therapist fits the patient with the rehabilitation device and configures initial parameters related thereto. For example, the therapist may access a user interface having one or more screen displays, such as those shown in FIGS. 3 and 4, to input one or more initialization parameters.

In certain embodiments, to aid in the rehabilitation process, a prosthetist also obtains certain demographic and/or physiological data relating to the user. For example, the prosthetist may gather information regarding the user's age, time since amputation, length of experience with a prosthetic device, weight, height, body mass index (BMI), combinations of the same or the like. Certain of these measurements may be obtained during an initial training session, while other of the variables may be collected during successive training sessions by the user. For example, the BMI of the user may be calculated during each training or gait analysis session to document any anthropometrical changes that may influence kinetic calculations for gait analysis.

At Block 510, the therapist selects a power level for the rehabilitation device, such as for example, to correspond to the needs and/or ability of the patient. In certain preferred embodiments, the therapist selects a power level for one or more of a plurality of rehabilitation-oriented functions. For example, the therapist may set an initial power level for at least one of the following: standing, sitting, ascending stairs, descending stairs, ascending ramps, and descending ramps. Such input may be received through a user interface, such as by accessing the appropriate tabs 320 and inputting data through the screen display 300.

At Block 515, the therapist determines if the power level of the rehabilitation device is at a maximum power level. In embodiments wherein multiple power levels are set, the prosthetist may determine if each of the selected power levels is at a maximum level. If the power level of the rehabilitation device is set at the maximum level, the rehabilitation process 500 proceeds with Block 520 wherein the patient continues to use the rehabilitation device at the maximum power level.

In certain embodiments, the "maximum power level" of the rehabilitation device may be patient-specific and may depend on different factors associated with the patient using the rehabilitation device. For instance, a maximum power level of a rehabilitation device for a 40-kilogram child may be less than a maximum power level of the rehabilitation device being used by a 100-kilogram adult.

In other embodiments, the maximum power level may correspond to a maximum default level of the rehabilitation device for a particular rehabilitation-oriented function. For example, a maximum power level for level-ground walking may correspond to the full propulsion capability of the rehabilitation device.

If the rehabilitation device is not operating at the maximum power level, the rehabilitation process moves to Block 525. At Block 525, the therapist observes the patient's use of the rehabilitation device, such as for example in a rehabilitation facility. In certain embodiments, the therapist may also analyze data automatically collected with respect to user movement and/or movement of the rehabilitation device. For example, a prosthetist may monitor the gait efficiency and/or biomechanical gait patterns of the amputee. In certain embodiments, for safety reasons, a sensitivity setting of the rehabilitation device may be reduced to a moderate or low level when the user leaves a training facility so as to avoid undesired triggering of a particular rehabilitation-oriented action by the rehabilitation device.

At Block 530, the therapist determines if the patient is conditioned for an increase in the power level of the rehabilitation device. For instance, the therapist may determine if the patient has rehabilitated to a point whereat the patient may comfortably handle an increase in the power of the rehabilitation device. If the patient is not ready for an increase in power of the rehabilitation device, the rehabilitation process 500 returns to Block 525, and the therapist continues his or her observation of the patient.

On the other hand, if the patient has rehabilitated to the point whereat the patient is ready for an increase in the power level of the rehabilitation device, the rehabilitation process 500 proceeds with Block 535, and the therapist increases the power level of the rehabilitation device. In certain embodiments, the therapist may increase the power level relating to one or more rehabilitation functions depending on the patient's ability in each of the functions. The rehabilitation process 500 then returns to Block 515 to determine if the increased power level is at a maximum power level of the rehabilitation device.

In certain embodiments, the rehabilitation process 500 for an amputee lasts for several weeks (e.g., 8 weeks), during which the patient may participate in several observation sessions (e.g., weekly sessions) with his or her therapist. Although the rehabilitation process 500 has been described with reference to particular embodiments, other acts or blocks may be used, or certain acts or blocks may be bypassed, in the rehabilitation of a patient. For instance, the rehabilitation process 500 may be performed without Block 505, such as with a patient who comes to a therapist pre-fitted with a rehabilitation device.

Figure 6:
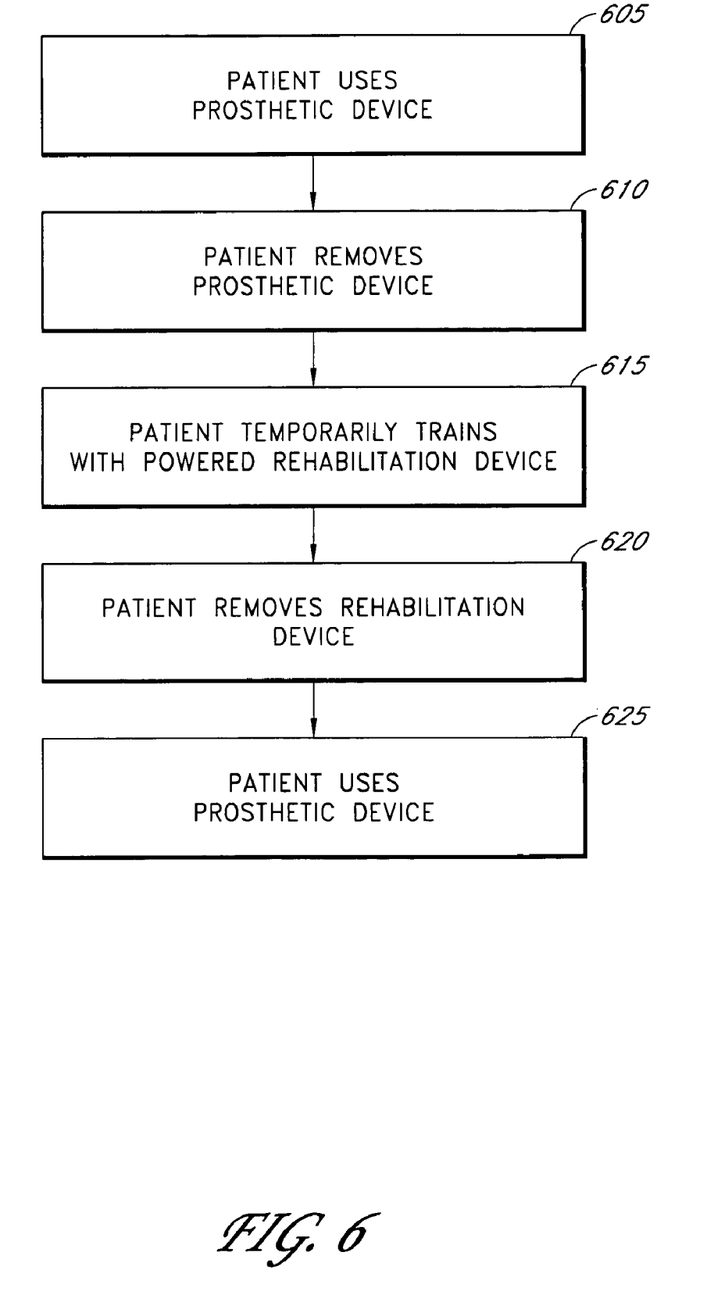
FIG. 6 illustrates an exemplifying embodiment of a flowchart of a training process involving a patient's temporary use of a powered rehabilitation device.

FIG. 6 illustrates an exemplifying embodiment of a flowchart of a training process 600 usable by a patient to train for using a second, passive-type prosthetic device. In particular, a patient may perform the training process 600 by temporarily using an adjustable-power rehabilitation device, such as the rehabilitation device 200 of FIG. 2. Such training allows the rehabilitation device to be temporarily used by, or rented by, multiple patients and provides a more cost-effective training process without requiring each patient to purchase a powered rehabilitation device. For exemplifying purposes, the following description of the training process 600 will be with reference to a rehabilitation device that comprises a powered prosthetic leg that simulates a natural, human gait and that is used to train an amputee how to walk more normally using a passive prosthetic leg. The rehabilitation device may also be used to help correct an unnatural gait developed by an amputee while using a more conventional prosthesis.

The training process 600 begins with Block 605, wherein a patient uses a passive prosthetic device. Such passive devices may include, for example, a prosthetic leg that is free swinging, dampening-controlled, and/or that is not power controlled and that rely upon the user's muscle function for movement. In certain embodiments, users of a RHEO KNEE provided by Ossur, a C-LEG® provided by Otto Bock, a free-swinging knee, or the like, may train with the powered rehabilitation device. At Block 610, the patient removes the passive prosthetic device and replaces the prosthetic device with a powered rehabilitation device.

At Block 615, the patient trains temporarily with the powered rehabilitation device. For example, the patient may use the rehabilitation device for a specific training period (e.g., a period of hours or days). Such training may, in certain embodiments, be under the supervision of a prosthetist and/or take place in a rehabilitation facility.

With respect to rehabilitation, the user may train periodically by walking with the powered rehabilitation device in an "off" or passive mode. This allows the user to further control the conditions under which he or she trains. For example, training may take place at a physical therapy facility or at a gym on an exercise machine, such as treadmill. In certain embodiments, the rehabilitation device alerts the user through an auditory, visual and/or vibratory alarm that the rehabilitation device is being powered off and/or entering a passive mode. Furthermore, in certain embodiments, when the rehabilitation device is powered off, the user is able to manually lock the device in a desired position.

At Block 620, the patient removes the powered rehabilitation device once he or she has completed her training session and returns to using his or her passive prosthetic device (Block 625). Preferably, the amputee is capable of using the passive prosthetic device to ambulate with a more natural gait developed from his or her training.

Although described with reference to particular embodiments, the training process 600 may be performed with more or fewer blocks or acts than those depicted in FIG. 6. For example, in yet other embodiments, the amputee may train with an embodiment of the powered rehabilitation device before substantial use of a more conventional prosthesis.

Figure 7:
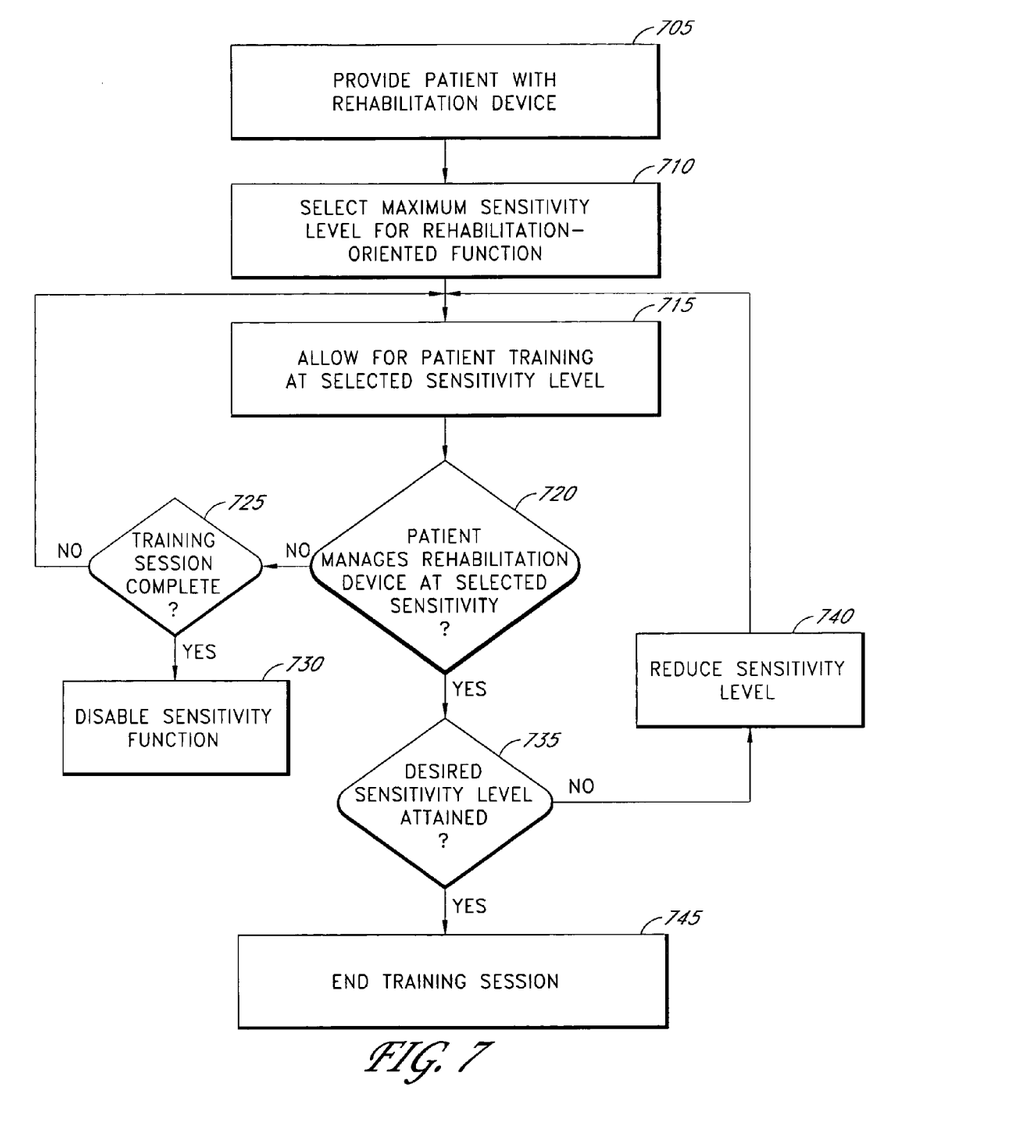
FIG. 7 illustrates an exemplifying embodiment of a flowchart of a sensitivity selection process for determining an appropriate sensitivity level of a powered rehabilitation device.

FIG. 7 illustrates an exemplifying embodiment of a flowchart of a sensitivity selection process 700 for determining an appropriate sensitivity level of a rehabilitation device according to the needs and/or abilities of a patient. In particular, a therapist may perform the selection process 700 to assist the patient in tuning a sensitivity level setting of a powered rehabilitation device, such as the rehabilitation device 200 of FIG. 2.

The sensitivity selection process 700 begins with Block 705 wherein a therapist provides a patient with a rehabilitation device. At Block 710, the therapist selects a maximum sensitivity level for a particular rehabilitation-oriented function (e.g., stair climbing). For instance, the therapist may enter the sensitivity selection through a user interface, such as one similar to the screen display 300 depicted in FIG. 4.

In certain embodiments, the maximum sensitivity level corresponds to relatively low effort and/or skill level of the patient needed to initiate the particular rehabilitation-oriented action. For example, the maximum sensitivity level may include the broadest range of sensed angle, pressure, and/or acceleration measurements that are capable of triggering the particular rehabilitation-oriented function.

For instance, a lower-limb rehabilitation device may be capable of automatically initiating a stair ascent function when a corresponding sensing module detects, among other things, the elevation of the user's healthy leg to a particular angle. The maximum sensitivity level for stair ascent locomotion may then correspond to the largest range of angular tilt that is capable of triggering the stair ascent function of the rehabilitation device.

In other embodiments, the maximum sensitivity level may correspond to the last sensitivity level achieved by the patient during his or her prior training session. Beginning training at a maximum sensitivity level also advantageously allows the patient to practice and/or fine-tune his or her movements to trigger a desired rehabilitation-oriented action by the rehabilitation device. In yet other embodiments, the selected sensitivity level may correspond to a plurality of rehabilitation-oriented actions.

At Block 715, the patient trains by using the rehabilitation device at the selected sensitivity level. For instance, the patient may train by repeatedly performing the particular rehabilitation-oriented action(s) associated with the selected sensitivity level. Such training, in certain embodiments, is preferably under the supervision of a therapist and/or takes place at a designated rehabilitation facility.

If the patient is not able to comfortably manage the operation of the rehabilitation device at the selected sensitivity level (Block 720), the sensitivity selection process 700 continues with Block 725. For instance, the therapist may determine that during the training period the patient unexpectedly triggered the particular rehabilitation-oriented action a relatively high number of times and/or was not able to consistently trigger the particular rehabilitation-oriented action when desired.

At Block 725, it is determined whether the current training session has been completed. If so, the therapist preferably turns off the sensitivity function of the rehabilitation device so that patient does not experience unexpected initiations of the particular rehabilitation-oriented function(s) while using the rehabilitation device at home and/or outside the training session (Block 730). However, if the current training session has not yet completed, the sensitivity selection process 700 proceeds with Block 715 wherein the user continues to train at the selected sensitivity level.

With reference back to Block 720, if the therapist determines that the patient has managed the rehabilitation device at the selected sensitivity level, the therapist may then determine if the desired sensitivity level has been reached (Block 735). For example, a desired sensitivity level may correspond to a sensitivity level that the therapist believes is safe for home use by the patient. In certain embodiments, the desired sensitivity level is a medium level that is less than the maximum sensitivity level but higher than the lowest available sensitivity level.

If the patient has not yet achieved the desired sensitivity level, the therapist may then reduce the sensitivity level of the rehabilitation device (Block 735), and the patient continues training at the lower sensitivity level (Block 715). For instance, in the example discussed above in Block 710 with respect to ascending stairs, reducing the sensitivity level may correspond to reducing the range of angular tilt that the user must achieve with his or her healthy leg to trigger a stair ascent function by the rehabilitation device.

However, if the patient has reached the desired sensitivity level, the training session may be terminated and the patient may be allowed to operate the rehabilitation device at the desired sensitivity level during home use (Block 745).

Although described with reference to particular embodiments, the sensitivity selection process 700 may be performed with more or fewer blocks or acts than those depicted in FIG. 7. For example, in yet other embodiments, the sensitivity selection process 700 may also include a selection of one or more adjustable power settings of the rehabilitation device during the user training. For instance, certain blocks of both FIGS. 5 and 7 may be performed during a training/rehabilitation session to determine both an appropriate power level and sensitivity level for one or more rehabilitation-oriented functions.

For exemplifying purposes, certain aspects of rehabilitation-oriented functions of a power rehabilitation device will now be described. In particular, the following disclosure provides examples of how a user may interact with a lower-limb rehabilitation device to perform certain rehabilitation-oriented actions.

Initiating Locomotion

In certain embodiments, while walking on a level surface or a ramp, the user may take a first stride with his or her healthy leg, touching the ground with the heel first. This contact with the ground is detected by a sensor. The user then brings his or her hip forward such that that rehabilitation device lifts off the ground and swings forward.

Sitting Down

In certain embodiments, the user shifts his or her body weight to the heels of both the healthy leg and the rehabilitation device. The user then bends both legs, in response to which the rehabilitation device may partially support the user as the user is lowering down. Once the rehabilitation device reaches a given or target flexion angle (e.g., representing a sitting position) for approximately 0.5 second, the device may automatically relax or enter a passive state.

Standing

In certain embodiments, the user leans slightly forward and places the forefoot of the rehabilitation device on the ground, using his or her hand to help bend the rehabilitation device if necessary. The user then places his or her weight on both the healthy leg and the rehabilitation device to begin standing, in response to which the rehabilitation device may assist the user while standing. If the user desires to sit down again, the user may stop the device extension for a certain length of time such that the rehabilitation device re-enters a passive state or allows for transition to the sitting position.

Transitions to and from Stairs

In certain embodiments, when ascending stairs, the user may first come to a stop and then elevate the healthy leg to the first step such that the forefoot of the healthy leg contacts the step. The user may then contact the next step with the forefoot of the rehabilitation device. The user transfers his or her weight onto the rehabilitation device, in response to which the rehabilitation device assists the user elevate. In yet other embodiments, the user may enhance the rehabilitation device's ability to detect stair ascent by exaggerating the lifting of the healthy foot on the first step and by bringing his or her body weight forward to the healthy side.

To stop ascending stairs, the user may place the healthy foot flat on the ground and avoid ground contact with the rehabilitation device for a certain length of time until a "stable" position is detected. In certain embodiments, to transition immediately from stair ascending to level or ramp walking, the user may reduce his or her locomotion speed when reaching the end of the stairs and contact the top step with the heel of the healthy leg. The rehabilitation device then detects level ground walking and adjusts accordingly.

In certain embodiments, when descending stairs, the user may first come to a stop and then begin descending the stairs by contacting the first step with the heel of the rehabilitation device. The user then transfers his or her body weight onto the rehabilitation device, in response to which the device performs a controlled flexion assisting the user down the step. The user brings his or her healthy leg forward by placing the forefoot of the healthy leg on the next step. The rehabilitation device then bends and actively swings forward to the next step. In certain embodiments, to stop descending the stairs, the user places the healthy foot flat on the ground and avoids ground contact with the rehabilitation device for a certain length of time until the "stable" position is detected. In situations where the user reaches the bottom of the stairs with the rehabilitation device first, the user may then take a very short step with the healthy leg heel. If the user reaches the bottom of the stairs with the healthy leg first, the user may then put his or her healthy foot heel-first on the ground and may take a long stride to swing the rehabilitation device more easily off the last step.

In yet other embodiments, such transitions with the rehabilitation device may be accomplished without the user coming to a full stop. For example, the rehabilitation device may detect a decrease in the acceleration of the user prior to transitioning to or from stairs.

While certain embodiments of the invention have been described, these embodiments have been presented by way of example only, and are not intended to limit the scope of the disclosure. For example, embodiments of the rehabilitation device described herein may comprise any prosthetic or orthotic device that utilizes an adjustable power range to facilitate movement of a user (e.g., hip, ankle, arm). Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the disclosure.

What is claimed is:

1. A training device for use with a limb of a patient, the training device comprising:
   an actively actuatable joint;
   an interface module configured to receive a selection of at least one of a plurality of power settings for determining power applied by the actively actuatable joint and a user selection of at least one of a plurality of sensitivity level settings to user motion for triggering automatic movement associated with one or more motions of the actively actuatable joint, wherein respective sensitivity level settings are associated with particular triggering levels of user motion; and
   a control module configured to output at least one control signal based at least on the at least one power setting selection and the at least one sensitivity level setting user selection, the at least one control signal being indicative of a power of the actively actuatable joint for at least partially replacing muscle function of the patient during a first category of motion of the training device, wherein the control module is configured to output the at least one control signal based at least on a comparison of a sensed user motion, detected by a sensing module, to the triggering level associated with the at least one sensitivity level setting user selection.

2. The training device of claim 1, wherein the power of the actively actuatable joint corresponds to a propulsion of the actively actuatable joint.

3. The training device of claim 1, wherein the actively actuatable joint is a knee joint.

4. The training device of claim 3, wherein the actively actuatable joint comprises an orthotic joint.

5. The training device of claim 1, wherein the interface module is configured to connect to a network.

6. The training device of claim 1, wherein the control module is further configured to output the at least one control signal based on physiological parameters of the user.

7. The training device of claim 1, wherein the interface module is further configured to receive a selection of one of a plurality of second power settings, wherein the plurality of second power settings corresponds to a second power of the actively actuatable joint during a second category of motion of the training device, the second category of motion being different than the first category of motion.

8. The training device of claim 1, wherein each of the plurality of sensitivity level settings is indicative of a predetermined range of sensed measurements required for triggering the first category of automatic motion of the training device.

9. The training device of claim 8, wherein the sensed measurements comprise at least one of sensed angle, pressure, and acceleration measurements.

10. The training device of claim 1, wherein the plurality of sensitivity level settings comprises at least one of a high, a medium and a low setting.

11. The training device of claim 1, wherein said comparison of a sensed user motion, detected by a sensing module, to the triggering level comprises determining that the sensed user motion attains the triggering level.

12. The training device of claim 1, wherein said comparison of a sensed user motion, detected by a sensing module, to the triggering level comprises determining that the sensed user motion corresponds to a range of triggering measurements associated with the triggering level.

13. A training device having propulsive capabilities, the training device comprising:
   an actively actuatable knee joint;
   a user interface module configured to receive a user selection of at least one of a plurality of sensitivity level settings to user motion for triggering automatic movement of the actively actuatable joint, wherein respective sensitivity level settings are associated with particular triggering levels of user motion;
   and an adjustable-power module configured to output one or more control signals for controlling an amount of power to be applied during a movement of the actively actuatable knee joint, wherein the adjustable-power module is configured to output the one or more control signals based at least on a comparison of a sensed user motion, detected by a sensing module, to the triggering level associated with the at least one sensitivity level setting user selection.

14. The training device of claim 13, wherein the adjustable-power module is further configured to output the one or more control signals based on at least one received physiological characteristic of a user.

15. The training device of claim 13, wherein the plurality of sensitivity level settings comprises a low sensitivity level setting and a high sensitivity level setting.

16. The training device of claim 15, wherein a user selection of the low sensitivity level setting requires a narrower range of at least one of sensed angle, pressure, and acceleration measurements of user motion than a user selection of the high sensitivity level setting to trigger the automatic movement of the actively actuatable knee joint.

17. The training device of claim 13, wherein the automatic movement corresponds to a category of motion selected from the group consisting of ascending stairs, descending stairs, ascending a ramp and descending the ramp.

18. The training device of claim 13, wherein the user interface module comprises a keypad.

19. The training device of claim 13, wherein the user interface module comprises a graphical user interface.

20. The training device of claim 13, wherein said comparison of a sensed user motion, detected by a sensing module, to the triggering level comprises determining that the sensed user motion attains the triggering level.

21. The training device of claim 13, wherein said comparison of a sensed user motion, detected by a sensing module, to the triggering level comprises determining that the sensed user motion corresponds to a range of triggering measurements associated with the triggering level.

* * * * *